(12) United States Patent
Khadem et al.

(10) Patent No.: US 9,002,076 B2
(45) Date of Patent: Apr. 7, 2015

(54) METHOD AND APPARATUS FOR OPTIMAL TRAJECTORY PLANNING

(75) Inventors: Rasool Khadem, Superior, CO (US); Jawad Mokhtar, Boulder, CO (US)

(73) Assignee: Medtronic, Inc., Minneapolis, MN (US)

( * ) Notice: Subject to any disclaimer, the term of this patent is extended or adjusted under 35 U.S.C. 154(b) by 1695 days.

(21) Appl. No.: 12/103,488

(22) Filed: Apr. 15, 2008

(65) Prior Publication Data

US 2009/0259230 A1 Oct. 15, 2009

(51) Int. Cl.
*G06K 9/00* (2006.01)
*A61B 19/00* (2006.01)

(52) U.S. Cl.
CPC ....... *A61B 19/5244* (2013.01); *A61B 2019/505* (2013.01); *A61B 2019/507* (2013.01)

(58) Field of Classification Search
CPC ........................................................ G06K 9/00
USPC ......................................................... 606/130
See application file for complete search history.

(56) References Cited

U.S. PATENT DOCUMENTS

| | | |
|---|---|---|
| 5,592,939 A | 1/1997 | Martinelli |
| 5,720,720 A | 2/1998 | Laske et al. |
| 5,913,820 A | 6/1999 | Bladen et al. |
| 5,983,126 A | 11/1999 | Wittkampf |
| 6,118,845 A | 9/2000 | Simon et al. |
| 6,201,988 B1 | 3/2001 | Bourland et al. |
| 6,381,485 B1 | 4/2002 | Hunter et al. |
| 6,390,097 B1 * | 5/2002 | Chandra ........................ 128/898 |
| 6,402,762 B2 * | 6/2002 | Hunter et al. ................. 606/130 |
| 6,474,341 B1 | 11/2002 | Hunter et al. |
| 6,482,182 B1 | 11/2002 | Carroll et al. |
| 6,493,573 B1 | 12/2002 | Martinelli et al. |
| 6,516,212 B1 | 2/2003 | Bladen et al. |
| 6,591,004 B1 | 7/2003 | VanEssen et al. |
| 6,697,534 B1 * | 2/2004 | Tan et al. ...................... 382/261 |
| 6,850,793 B1 | 2/2005 | Miyazaki et al. |
| 6,905,492 B2 | 6/2005 | Zvuloni et al. |
| 7,081,088 B2 | 7/2006 | Geiger |
| 7,167,180 B1 | 1/2007 | Shibolet |
| 7,190,163 B2 | 3/2007 | Rajagopalan et al. |
| 7,217,276 B2 | 5/2007 | Henderson et al. |
| 7,542,791 B2 * | 6/2009 | Mire et al. .................... 600/407 |
| 7,555,331 B2 * | 6/2009 | Viswanathan ................ 600/424 |
| 7,623,736 B2 * | 11/2009 | Viswanathan ................ 382/293 |
| 7,657,075 B2 * | 2/2010 | Viswanathan ................ 382/132 |
| 7,756,308 B2 * | 7/2010 | Viswanathan ................ 382/128 |
| 7,840,256 B2 * | 11/2010 | Lakin et al. .................. 600/426 |
| 8,116,847 B2 * | 2/2012 | Gattani et al. ................ 600/424 |
| 8,504,285 B2 * | 8/2013 | Vepsalainen .................. 701/410 |
| 2003/0114752 A1 | 6/2003 | Henderson et al. |

(Continued)

OTHER PUBLICATIONS

Hadani et al., Novel, Compact, Intraoperative Magnetic Resonance Imaging-guided System for Conventional Neurosurgical Operating Rooms, Neurosurgery, vol. 48, No. 4, Apr. 2001.*

(Continued)

*Primary Examiner* — Michael Fuelling
(74) *Attorney, Agent, or Firm* — Harness, Dickey & Pierce, P.L.C.

(57) ABSTRACT

A system and method can increase confidence or other factors of a trajectory, path, etc. for a procedure. The system can use various weighting or determining factors to identify confidence of identified trajectories. The identified trajectories can be used for various purposes, such as diagnosis or treatment.

23 Claims, 7 Drawing Sheets

(56) References Cited

U.S. PATENT DOCUMENTS

| | | |
|---|---|---|
| 2004/0010190 A1* | 1/2004 | Shahidi .................. 600/407 |
| 2004/0215071 A1 | 10/2004 | Frank et al. |
| 2005/0004617 A1 | 1/2005 | Dawant et al. |
| 2005/0049486 A1 | 3/2005 | Urquhart et al. |
| 2005/0085714 A1 | 4/2005 | Foley et al. |
| 2005/0085720 A1 | 4/2005 | Jascob et al. |
| 2005/0171558 A1 | 8/2005 | Abovitz et al. |
| 2005/0267360 A1 | 12/2005 | Birkenbach et al. |
| 2006/0084867 A1 | 4/2006 | Tremblay et al. |
| 2006/0235483 A1 | 10/2006 | Schwan |
| 2007/0100226 A1 | 5/2007 | Yankelevitz et al. |
| 2007/0156453 A1* | 7/2007 | Frielinghaus et al. ............ 705/2 |
| 2007/0167788 A1 | 7/2007 | Hartlep et al. |
| 2007/0244387 A1 | 10/2007 | Rodriguez Ponce et al. |
| 2007/0249911 A1 | 10/2007 | Simon |
| 2007/0276340 A1 | 11/2007 | Poston et al. |
| 2008/0081982 A1 | 4/2008 | Simon et al. |
| 2008/0097165 A1* | 4/2008 | Gattani et al. ................ 600/300 |
| 2008/0097187 A1 | 4/2008 | Gielen et al. |
| 2008/0097287 A1 | 4/2008 | Nelson et al. |
| 2008/0123921 A1 | 5/2008 | Gielen et al. |
| 2008/0123922 A1* | 5/2008 | Gielen et al. ................ 382/131 |
| 2008/0123923 A1 | 5/2008 | Gielen et al. |
| 2008/0132909 A1 | 6/2008 | Jascob et al. |
| 2010/0240986 A1 | 9/2010 | Stiles |

OTHER PUBLICATIONS

"Cranial Oncology Procedure Solutions and Benefits," Medtronic, 2 pages, http://www.medtronicnavigation.com/procedures/cranial/cranial_oncology.jsp, printed Mar. 13, 2008.

Butz et al. Pre- and Intra-operative Planning and Simulation of Percutaneous Tumor Ablation, Proceedings of the Third International Conference on Medical Image Computing and Computer-Assisted Intervention, p. 317-326, Oct. 11-14, 2000.

Champleboux et al., "Accurate Calibration of Cameras and Range Imaging Sensors: the NPBS Method," IEEE International Conference on Robotics and Automation, Nice, France, May 1992.

Schueler et al., "Correction of Image Intensifier Distortion for Three-Dimensional X-Ray Angiography," SPIE Medical Imaging 1995, vol. 2432, pp. 272-279.

Wood et al. Technologies for Guidance of Radiofrequency Ablation in the Multimodality Interventional Suite of the Future. J Vasc Interv Radiol. Jan. 2007; 18(1 Pt 1): 9-24. doi:1 0.1 016/j.jvir.2006.1 0.013.

* cited by examiner

METHOD AND APPARATUS FOR OPTIMAL TRAJECTORY PLANNING

FIELD

The present teachings relate generally to navigation systems for surgery and particularly to a system and associated methods for determining and illustrating planned and actual paths for an instrument during a surgical procedure.

BACKGROUND

The statements in this section merely provide background information related to the present disclosure and may not constitute prior art.

A surgical procedure can be performed for various purposes. For example, a surgical procedure on a portion of the brain or other neurological structures can be performed. Generally, access to the brain and other neurological structures, however, is restricted and a substantially open procedure is not selected. A navigation system can be used to navigate and guide movement of an instrument relative to a neurological structure when direct access or view of an anatomical area is restricted.

Image data of a patient can be selected for viewing by a user, such as a surgeon, for planning a procedure. During the planning of the procedure, however, the surgeon generally illustrates a plan or selected path based upon the surgeon's knowledge or identification of various structures of the anatomy. The surgical procedure, once the planning is completed, can then proceed based upon the planning. Nevertheless, the planning of the procedure may be limited by the image data acquired, experience of the surgeon, or other limitations.

SUMMARY

A computer navigation system or surgical navigation system can be provided to navigate a surgical procedure relative to a patient. Combined with or separate from the navigation system, however, can be a planning system. The planning system can be used to plan or determine various parts of a procedure, such as planned trajectories of an instrument during a procedure and/or prior to a procedure. The planning system can use any selected information. Information can include atlas models of the anatomy, patient specific data (e.g. image data or medical history data, etc.), surgeon knowledge, statistical data (i.e. of multiple medical procedures, anatomical study, etc.) and other information for planning a procedure. Planning of the procedure can then procedure based upon the various information supplied to the planning system.

According to various embodiments, a method of determining a cost value for a selected procedure includes providing data regarding a patient and determining a plurality of trajectories for use in the procedure. The method can further include determining a cost function for at least a portion of at least one of the plurality of the trajectories. A cost function value representation of an area defined by the plurality of determined trajectories can be output, such as for human viewing.

According to various embodiments, a method of determining a cost function value for a selected procedure can include acquiring image data of the patient, determining anatomical features in the acquired image data, and associating a weight to each of the determined anatomical features. A plurality of possible trajectories through an anatomical region of the patient can be determined and a cost function for each of the plurality of trajectories can further be defined or determined. A graphical representation of a cost function value of the cost function for each of the plurality of the trajectories can be output for a user.

According to various embodiments, a system for illustrating a graphical representation of a trajectory can include various components or elements. The system can include a first processor operable to execute instructions to determine a cost of a trajectory for a procedure and a display device operable to display a graphical image, wherein the display device is operable to display the trajectory and the associated determined cost value. The cost value can be displayed as a graphical representation with the display device.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. Moreover, while the present disclosure is specifically directed to determining and illustrating trajectories in a neural procedure, any appropriate procedure may be planned and illustrated.

Figure 1:
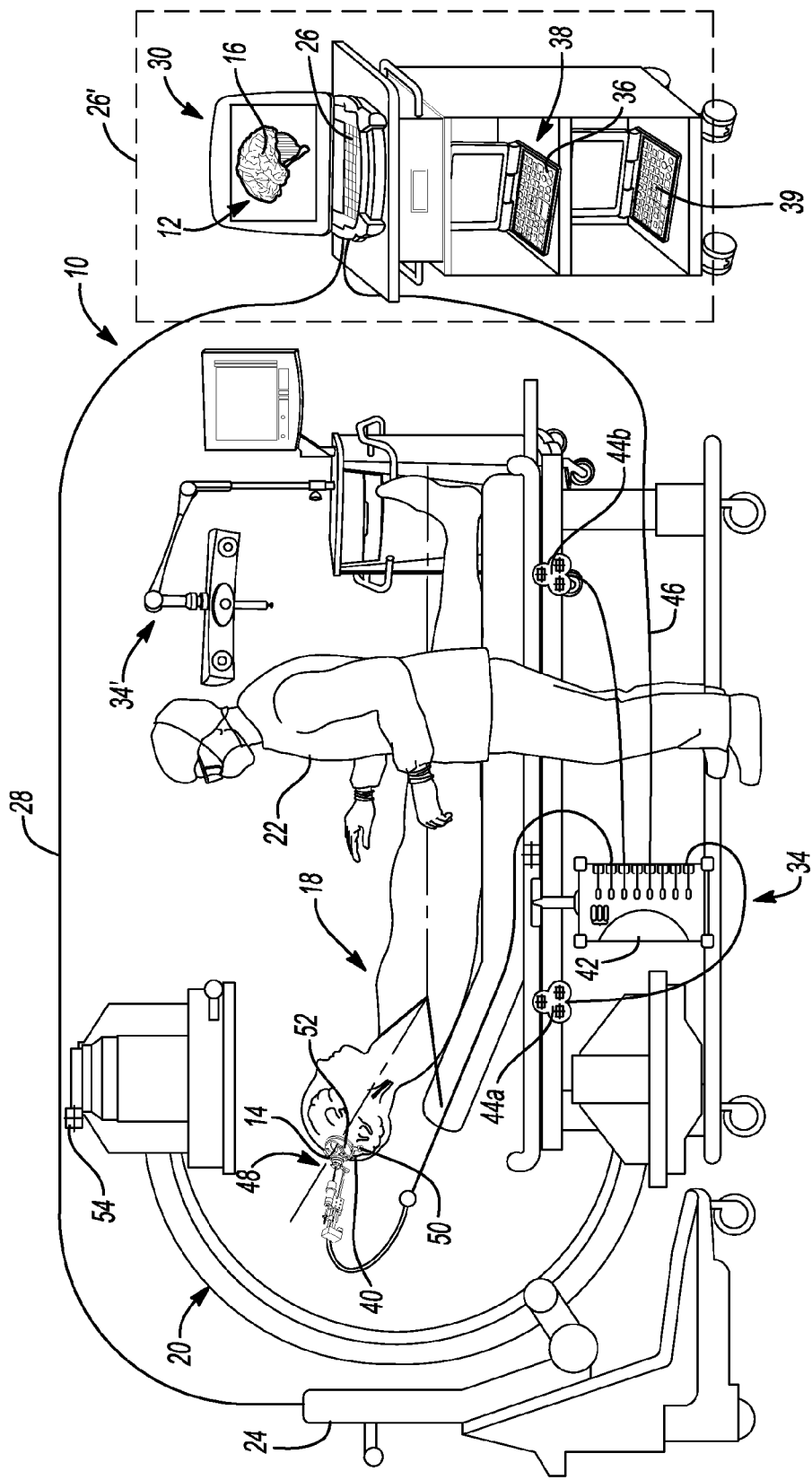
FIG. 1 is an environmental view of a surgical navigation system according to various embodiments.

A guided or navigated procedure can be performed with a navigation system 10, illustrated in FIG. 1. The guided procedure can be any appropriate procedure, such as a neural procedure, spinal procedure, or an orthopedic procedure. The navigation system 10 can include various components, as will be discussed further herein. The navigation system 10 can allow a user, such as a surgeon, to view on a display 12 a relative position of an instrument 14 in a coordinate system. The coordinate system can define a patient space or navigation area defined relative to a patient 18. The display 12 can display a representation of an instrument 14 that is in patient space relative to the image data, defining image space, or only in relation to another graphical representation, such as in an imageless system.

A procedure, as discussed further herein, can be performed using or being assisted with the image data. The image data can be image data acquired of the patient 18 using any appropriate imaging system, such as an x-ray imaging system 20. The imaging system can also include a Magnetic Resonance Imager (MRI) imaging system. The MRI imaging system can be used to acquire both image data and diffusion data relating to the patient 18. The image data including diffusion data can also be referred to as gradient image data. The various types of data can be used to create images for viewing on the display 12. The image data can be used by a user or surgeon 22, such as during a navigated procedure. The various types of data, such as the diffusion data, can be further used to illustrate tracts alone or tracts relative to the image data 16 acquired of the patient 18.

The navigation system 10 can be used to navigate or track the instrument 14 including: catheters, probes, needles, guidewires, implants, deep brain stimulators, electrical leads, etc. The instrument 14 can be used in any region of the body. Also, any appropriate information about the instrument 14 can also be displayed on the display 12 for viewing by the surgeon 22. The display may include a graphical representation of the instrument 14 and other information, such as trajectory information.

Although the navigation system 10 can include the exemplary imaging device 20, one skilled in the art will understand that the discussion of the imaging device 20 is merely for clarity of the present discussion and any appropriate imaging system can be used. The navigation system 10 can also be used in combination with patient specific data and non-patient specific data. Image data can be patient specific data that is captured or obtained at any appropriate time with any appropriate device.

The navigation system 10 can include the optional imaging device 20 that is used to acquire pre-, intra-, or post-operative or real-time image data of the patient 18. The imaging device 20 can be an x-ray C-arm having an x-ray source and an x-ray receiving section, computed tomography systems, etc. Any appropriate MRI system that can collect diffusion data can be used, as discussed herein. The imaging device 20 can be provided to acquire image data 16 of the patient 18 prior to or during a procedure for diagnosis of the patient 18.

The optional imaging device 20 can further be any appropriate 2D, 3D or 4D imaging modality. For example, an isocentric fluoroscopy, bi-plane fluoroscopy, O-ARM® imaging device (sold by Medtronic Navigation, Inc. having a place of business in Colorado, USA), ultrasound, computed tomography (CT), T1, weighted magnetic resonance imaging (MRI), T2, weighted MRI, positron emission tomography (PET), optical coherence tomography (OCT), single photon emission computed tomography (SPECT), or planar gamma scintigraphy (PGS) may also be used.

Although FIG. 1 illustrates an environmental view showing both the patient 18, surgeon 22, navigation system 10, and other elements, it will be understood that this is merely exemplary of all the portions that can be provided together. For example, an electromagnetic navigation or tracking system may not be provided in a room with a MRI Magnetic Imaging System.

An imaging device controller 24 can control the imaging device 20 to capture and store the image data for later use. The controller 24 can be used intra- or pre-operatively to control and obtain image data of the patient 18. The controller 24 may also be separate from the imaging device 20.

The image data can then be forwarded from the controller 24 to a processor system 26, via a communication system 28. The communication system 28 can be wireless, wired, a data transfer device (e.g. a CD-Rom or DVD-Rom), or any appropriate system. A work station 30 can include the processor system 26, the display 12, a user interface, and a memory. It will also be understood that the image data is not necessarily first retained in the controller 24, but may be directly transmitted to the workstation 30 or to a tracking system 34, as discussed herein.

The workstation 30 provides facilities for displaying the image data 16 as an image on the display 12, saving, digitally manipulating, or printing a hard copy image of the received image data. The user interface, which may be a keyboard, mouse, touch pen, touch screen or other suitable device, allows a surgeon or user to provide inputs to control the imaging device 20, via the controller 24, or adjust the display settings of the display 12. The user 22 can interact with the workstation 30, via the user inputs at any appropriate time to perform various functions and give specific instructions to the system for processing.

The processor system 26 can process various types of data such as image data provided in the memory or from the imaging system 20. The processor system 26 can process navigation information, such as information provided from the tracking system 34, 34'. In addition, navigation processing can include determining a position of the tracked instruments relative to the patient 18 for display relative to the image data 16 on the display 12. The processor system 26 can also include a confidence system or cost function processor 36, in a second work station 38. A processor 39 is also operable to associate a weight with anatomical features in the image data, as discussed herein. It will be understood that each of the processing portions 26, 36, 39 can be processed by separate or individual processors or can be processed substantially sequentially or in any appropriate manner with a single appropriate processor, exemplary illustrated by single processor phantom box 26'.

The image data obtained of the patient 18 can be used for various purposes. The image data can be obtained for performing a navigated procedure relative to the patient 18, planning an operation or procedure on an anatomy, and other appropriate reasons. For example, during a neurological procedure, it can be selected to obtain image data of a brain 40 of the patient 18 for viewing during the procedure and navigating the instrument 14 relative to the image data 12. Further, the acquired image data can be used to plan the movement of the instrument 14 or for positioning an implant during an operative procedure.

The navigation system 10 can include the electromagnetic tracking system 34. The tracking system 34 can include an interface system or box 42 that can interface with one or more electromagnetic field generating localizers 44a, and 44b. A communication portion 46 can interconnect the interface 42 with the workstation 30. The interface or communication can be wireless, wired, or any appropriate communication.

The interface portion 42 can further communicate with a tracking sensor 48 associated with the instrument 14. According to various embodiments, the tracking sensor 48 can be connected directly to the instrument 14, be integrated into the instrument 14, or in any appropriate configuration. In addition, a dynamic reference frame 50 can be interconnected with the patient 18 in any appropriate manner, such as connected rigidly to a guide device 52, if selected. Various headframes include the Leksell® Headframe. Various other guiding systems can include the Navigus® frame or guide system sold by Medtronic, Inc. It will be understood that any appropriate guide system can be used, and these are merely exemplary. Alternatively, the dynamic reference frame 50 can also be interconnected with the patient 18 in any appropriate location or manner to maintain a registration of the patient 18 with the coordinate system of the tracking system 34 and the image data 16 (i.e., image space), or any appropriate registered portion. Other tracking sensors, such as an imaging system tracking sensor 54 can be interconnected with the imaging system 20 to determine the location of the imaging system, or a portion thereof, relative to the patient 18.

It will also be understood that any appropriate tracking system can be provided. In addition to or an alternative to the electromagnetic tracking system 34, an optical tracking system 34' can be provided. It will be further understood that acoustic tracking system, radiation tracking system, acceleramator tracking system, electrical potential, or any appropriate tracking system can be used with the navigation system 10. The tracking system 34, 34' can be used to track the patient 18, instrument 14, or any appropriate portion in the navigation system 10.

The tracking system 34, 34' can track the position of any tracking sensor and communicate the position of the tracking sensor to the work station 30. The workstation 30, either alone or in combination, with a processor of the tracking system 34, 34' can determine a position of the tracking sensor that is tracked with a tracking system relative to the patient 18 (i.e., patient space) and correlate that position relative to the image data 16 (i.e., image space). The correlation can be performed due to a registration of the patient 18 to the image data 16 or to a space in which tracking occurs.

Registration of the patient 18 to the image data 16, or any appropriate system (e.g., an imageless tracking procedure) can be performed in any appropriate manner. For example, contour matching, point registration, surface registration, or any appropriate registration system can be used. Various registration systems or methods can be used with the optical tracking system 34' and are incorporated within various tracking systems, such as the Stealthstation® Treon® Tracking System and Stealthstation® Tria® Tracking System, both sold by Medtronic Navigation, Inc. Various registration systems or methods can also be used with the electromagnetic tracking system 34, which can include the StealthStation® AXIEM™ electromagnetic (EM) tracking System, also sold by Medtronic Navigation, Inc. Appropriate tracking and registration procedures are also disclosed in U.S. patent application Ser. No. 11/607,762 filed Dec. 1, 2006, and published as U.S. Pat. App. Pub. 2008/0132909 on Jun. 5, 2008, incorporated herein by reference.

As discussed further herein, the tracking systems 34, 34' as a part of the navigation system 10 can be used to track the position of the instrument 14. Tracking the position of the instrument 14 can be used to determine that the instrument 14 is being positioned relative to the patient 18 according to a predetermined or planned trajectory. In addition, the navigation system 10 can be used to illustrate a predetermined or planned trajectory and the position of the instrument 14 relative to the illustrated plan. The navigation system 10 can also provide an indication to the surgeon 22 of whether the preplanned trajectory is being adhered to, any alterations that are being made or may be required during a procedure, or other appropriate indications.

The planning and navigation system 10, as exemplary discussed above, can be used to plan a procedure and further perform a procedure on the patient 18. The planning system can include the planning processor 36 that can be used to determine a cost function or weight various trajectories. The trajectories and associated weights and costs can be displayed on the display 12. For example, as discussed further herein, in a procedure performed on the brain 40 of the patient 18, the planning system can illustrate various entry points, target points, and trajectories between the entry and target points. The system can further determine a cost function or appropriateness factor for each of the selected trajectories, entry points, and target points. It will be understood by one skilled in the art that other feature or procedure portions can also be determined and associated costs associated therewith by the planning system, such as guide placement, length of path, time of procedure, etc.

Figure 2A:
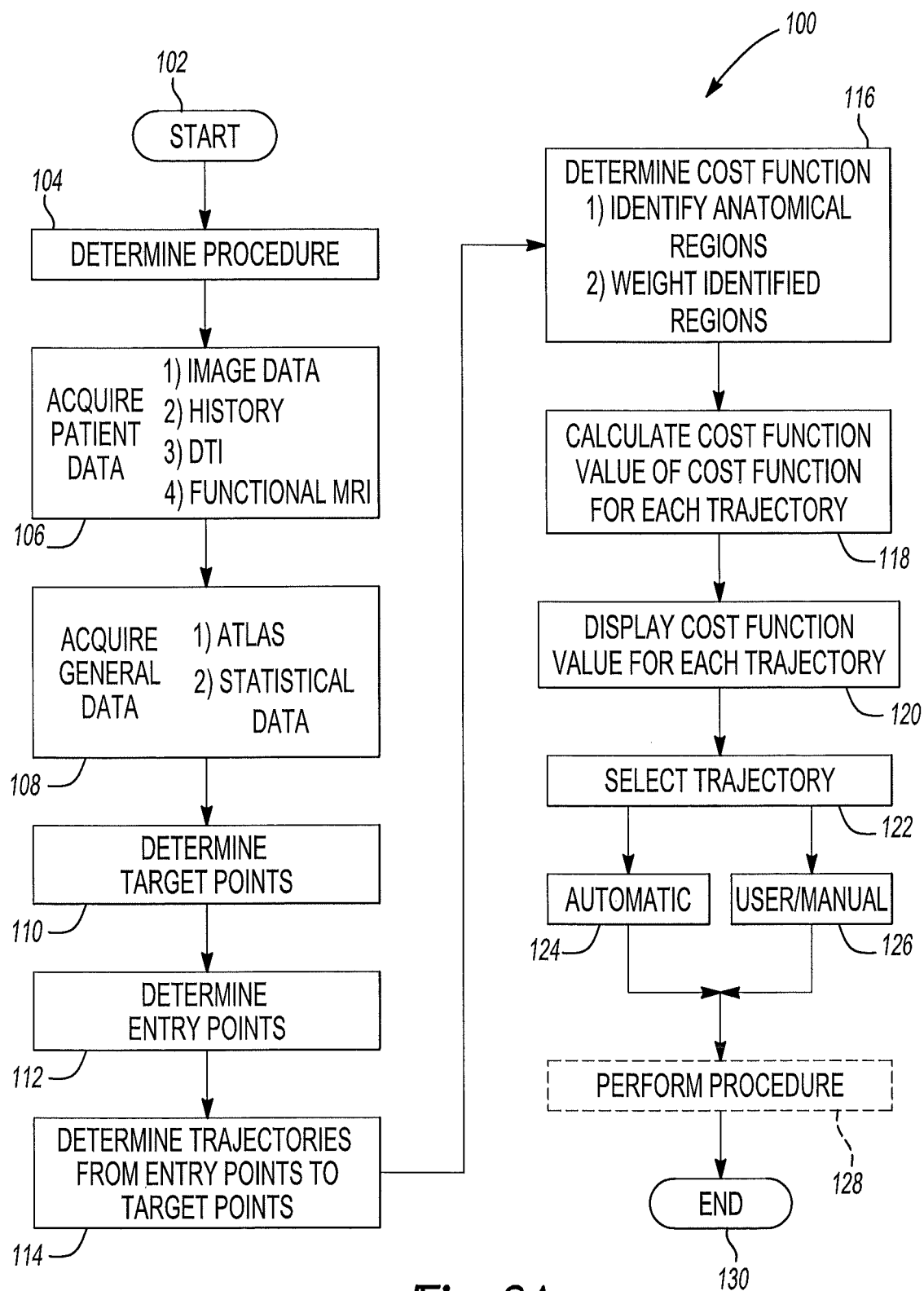
FIGS. 2A and 2B are flow charts illustrating various portions of a method of planning and illustrating planning of a procedure.
Figure 2B:
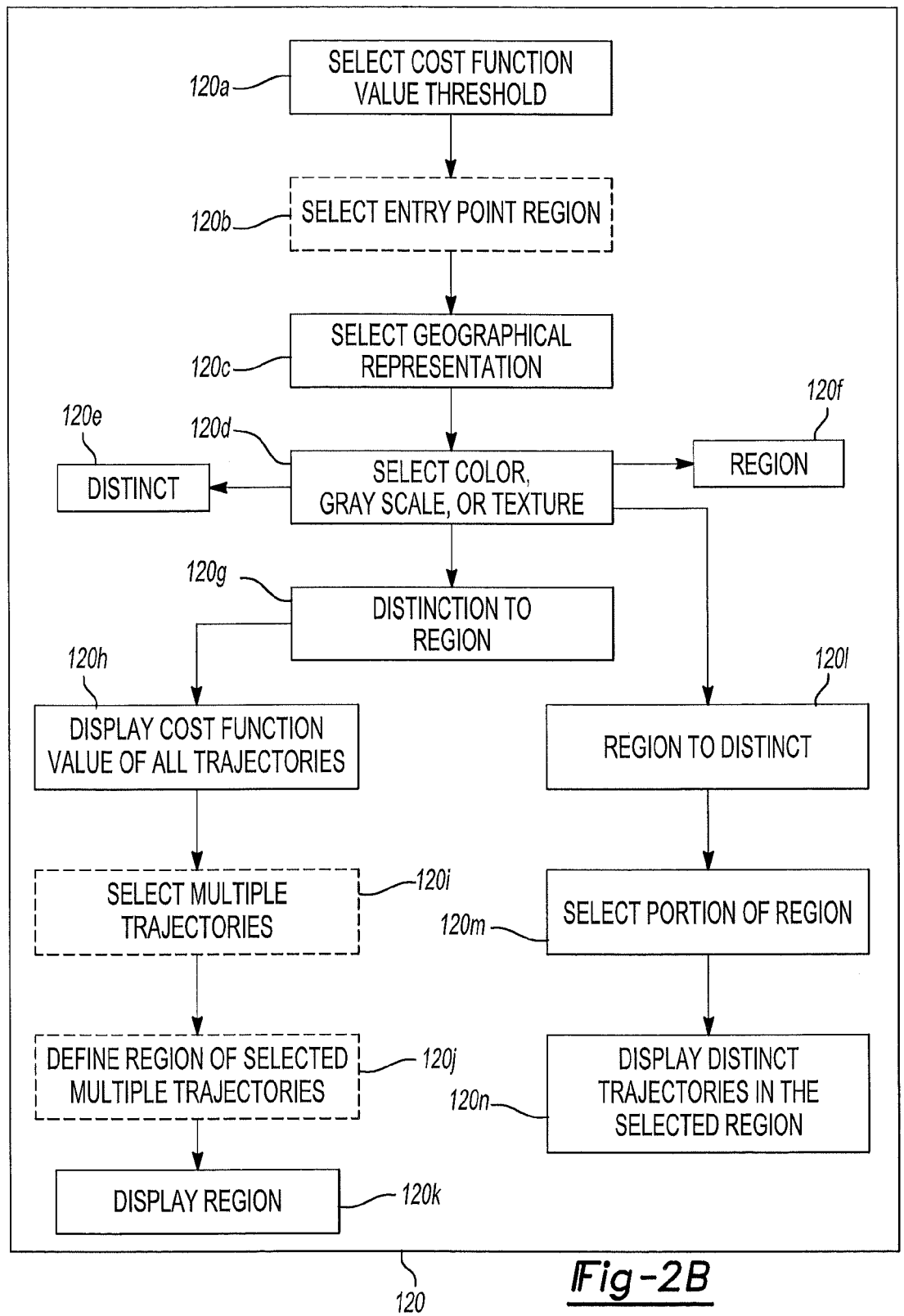

With reference to FIGS. 2A and 2B, a method 100 of determining or illustrating a cost value for various entry points, target points, and trajectories is illustrated. The method 100 can begin in start block 102. The method can then proceed to determining a procedure in block 104. Determining the procedure in block 104 can also be determinative of various additional portions of the method 100. For example, acquiring patient data in block 106 can depend upon the determined procedure in block 104. If the determination procedure is a neurological procedure, acquiring patient data can include acquiring patient data of a head region, including MRI data and the like. Alternatively, if determining the procedure in block 104 is a pedicle screw placement procedure, then determining the patient data in block 106 can include image data of a spinal region of the patient.

Acquiring patient data in block 106 can include acquiring various types of data. For example, as briefly discussed above, image data can be acquired of the patient 18. The image data can include any appropriate type of image data including MRI image data, CT image data, PET image data, and the like. Further, various data can include diffusion tensor image data, functional MRI data, and other functional imaging procedures. Other patient data can also include current or past history of the patient, such as prior procedures, medical history, and the like. The acquired patient data can be used in a cost function, discussed further herein, to determine a cost value for various planning procedures.

Also, general data or statistical data can be acquired in block 108. The general data can include atlas image data of a region relating to the determined procedure in block 104. For example, if the determined procedure is a neurological procedure, acquired general data can include an atlas map of the brain. In addition, statistical data, such as average positions of various anatomical features, and other statistical information can also be acquired in the general data in block 108. Again, the general data acquired in block 108 can be used in the cost value function discussed further herein.

Once appropriate data is acquired of the patient in block 106 and other data in block 108, if desired, a determination of a procedural or anatomical target point can be performed in block 110. The determined anatomical target point from block 110 can include one or more anatomical target points for a selected procedure. Anatomical target points can include any appropriate anatomical target points, such as the position of a pedicle screw, the position of an implant (e.g. a deep brain stimulation probe or a catheter lead). The anatomical target points can be determined based upon the data acquired of the patient and other appropriate data, such as the general data acquired in block 108. The anatomical target points can also relate to other procedures, such as the position of a tumor or growth, including a tumor in the brain of the patient 18. The anatomical target point can include one or more points as defined by the anatomy and can be represented as image or virtual target points in the data acquired of the patient 18 in block 106. For example, the virtual target points can include one or more voxels in three dimensional image data or portions of a voxel from three dimensional image data. It will be understood, that an anatomical target point can be determined based on image or other data and the anatomical target point can then be represented on a display device relative to the image data as a virtual target point.

A determination of an entry point can be made in block 112. The entry points in block 112 can be points of entry to reach the determined target points in block 110. The entry points can include incision areas, burr hole creation areas, and other appropriate entry points. The determination of the entry points in block 112 can be based upon any appropriate data, such as the determined anatomical target points in block 110, or patient data in block 106, or even data from the general data in block 108. The entry point or entry points selected for analysis can include a limited number of points or all possible points (e.g. an entire area of a skull). Similar to target points, the entry points can be anatomical entry points which can then be illustrated as virtual image points. Discussion of a an entry point or target point will be understood to include both types, unless specifically indicated otherwise.

As illustrated in FIG. 1, a burr hole can be created to allow an instrument to be guided into the brain 40 of the patient 18. The determined entry points can include one or more possible burr hole locations on a skull of the patient 18 to reach the anatomical target point within the brain 50 of the patient 18. The determination or selection of one or more burr holes can be based upon prior history of the patient, determined in block 106, such as prior burr hole formation, implant position, and the like.

Once the target points, anatomical or virtual, have been determined in block 110 and entry points have been determined in block 112, trajectories can be determined in block 114. Trajectories can include any path that interconnects the target points and the entry points. For example, if one target point and one entry point is determined a trajectory can include a straight line or curved line connecting the one target point and the one entry point. In addition, if multiple target points and one entry point is determined, then the determined trajectories in block 114 can include a straight or curved line between each of the target points and the one entry point. Similarly, for multiple entry points and a single target point, multiple trajectories can be defined. Finally, for multiple target points and multiple entry points, trajectories can include each of the trajectories that interconnect each of the target points and each of the entry points. Therefore, each entry point can include trajectories to each of the target points and each of the target points can include trajectories to each of the entry points. The number of trajectories determined in block 114 can be substantially large.

The trajectories determined in block 114 can be based upon various information, such as the instrument that will move along the trajectory, the guiding system, and other appropriate information or limitations. For example, if a rigid instrument is to be used in the determined procedure, for example an instrument that is unable to curve, then only straight trajectories will be determined from the entry point to the target point. The type of instrument can also be included in the general data acquired in block 108.

A cost function can then be determined in block 116. It will be understood, however, that various portions of the cost function can be determined prior to determining target points in block 110, determining entry points in block 112, or determining trajectories in block 114. For example, determining cost functions can include determining anatomical regions or identifying anatomical regions, weighting the identified regions, and other appropriate information. The determined cost function can include an algorithm to determine a cost value that can be applied to each of the determined entry points, target points, and trajectories discussed above. Weighting for the cost function can vary based upon the determined procedure in block 104 and can be selected by a user for various procedures. Weighting, however, can be the specific values or factors that are assigned or associated with specific regions or areas, such as entry points or vascular regions. The weights can then be incorporated into a cost function. The cost function, in turn, can then be calculated to determine a cost value for a specific trajectory, entry point, target point, etc.

Weighting for the various cost functions can include negative values or negative costs being applied to trajectories, entry points, and target points that intersect or traverse near anatomical portions, including vascular or sulci regions in the brain. Weighting or factors can also be applied to any anatomical region, such as white matter, grey matter, fiber tracts, nerve bundles, etc. These regions can be automatically segmented or partially or completely identified by the user 22.

Various examples are provided further herein, but a cost function can include a summation of each cost factor applied to each of the anatomical portions or regions identified in the patient data, such as image data, history, or statistical or atlas data. In other words, a cost function may include a summation of all cost factors relating to a trajectory that is identified to pass near, for example, a vascular region, a fiber tract, and be 10, millimeters long. The cost function value can be illustrated on the display 12, as discussed further herein, for viewing and analysis by a user. Other cost function values can also be displayed on the display 12, such as for other trajectories that are determined to traverse or pass near various other anatomical features, such as one or more fiber tracts, vascular regions, or the like. Regardless of the number of trajectories determined, the cost function can be identified for each of the trajectories as a summation of each of the weights or factors associated with each of the anatomical portions identified in the patient data and provided for use by as user. The graphical representation can then be associated with each cost function value and illustrated on the display 12.

In addition, varying cost values can be applied to trajectories, entry points, or target points that are at various distances from vascular regions or sulci. For example, a negative value ten (−10) can be applied to a trajectory that directly intersects a vascular region while a negative value five (−5) may be applied to a trajectory that passes within one millimeter (1, mm) of a vascular region and a negative value one can be applied to a trajectory that is at least two millimeters (2, mm) away from a vascular region. Therefore, a cost function value is not a fixed value, or need not be a fixed value, but can vary based upon information from the determined trajectories, entry points or target points and based upon the patient data.

Other cost factors or weights can include distance from determined fiber tracts, such as fiber tracts identified using diffusion tensor image data. Fiber tracts, as generally understood in the art, can identify or be the anatomical portions of the anatomy that represent connections within the brain or other neural regions. Therefore, a trajectory near a fiber tract may be assigned a negative weight in a cost function as opposed to one that does not come near or traverse a fiber tract. Other weights or cost factors can include a distance to travel along the trajectory from the entry point to the target point. For example, a more negative cost factor can be given to a trajectory that includes a longer path. Also, a burr hole or entry hole or point cost factors can be applied. For example, the positioning of a burr hole at one portion on the skull can be more advantageous or desirable than positioning a burr hole at another location on the skull. Therefore, the determination of entry points in block 112 can be given different cost values. Also, cost factors to two different target points can be assigned. For example, a tumor in the brain can include a selected size or shape. Although it can be selected to obtain a biopsy from any appropriate portion of the tumor, it could be selected to give a higher cost factors to a selected region of the tumor than to another region.

The weights or cost factors can be determined by the user 22 or the planning system 38. For example, in block 118 cost factors can be predetermined for various anatomical portions that are identified manually or automatically with the system. In other words, the image data can be presented on the display 12 and the user 22 can select various areas as anatomical portions. The user can then assign a weight or cost factor to each of the identified anatomical portions. Alternatively, or in addition to the user input, the planning system 38 or any appropriate processor system associated with the planning system 38, can automatically (i.e. based on a program algorithm) identify anatomical portions and assign cost factors or weights to the anatomical portions identified. The planning system 38 can automatically identify vascular portions and assign a value as a cost factor to each of the portions. In addition, the planning procedure 100 can also include a gradient cost factor determination based upon the distance of a trajectory from the identified anatomical portion. Therefore, as discussed above, the planning system 38 can also automatically identify the weight that will be applied to each of the cost factors or weights depending upon the location of the trajectory relative to each of the anatomical portions for determining a cost function value for each of the trajectories. Also, the display 12 can display an average cost function value for an entire trajectory, portion of a trajectory, or region of trajectories (which can be formed by a plurality of trajectories.)

The cost function value can then be calculated in block 118 based on the cost function. It will be understood that the cost function value can be any appropriate value and the discussion herein that a positive cost function value is more selectable or desirable for a selected procedure is merely exemplary. Nevertheless, the cost function value calculated in block 118 can be based upon the cost function determined in block 116 including weights or factors of the determined target points in block 110, the determined entry points in block 112, or determined trajectories in block 114. Also, the determination of cost functions in block 116 can include identification of anatomical features or structures in the acquired patient data in block 116 or the acquired general data in block 108. Therefore, the calculation of the cost function value can determine the cost function value for each of the selected data, including the trajectories, entry points, target points, patient data, general data, and output cost value for each selected part of the data.

The cost function value can then be output in block 120. The output in block 120 can include any appropriate output. For example, the output can be a graphical representation of the cost function values assigned to any of the selected data. For example, a cost function value can be illustrated for each of the target or entry points and each of the trajectories. The cost function value can be any value for reference for the user 22. For example, a large number can convey a prohibitive trajectory while a low cost function value can convey a favorable trajectory. It will be understood, however, that positive, negative, and appropriate ranges of numbers can be used to convey appropriate or selected information.

With reference to FIGS. 3-5C, as discussed further herein, various entry points, trajectories, and target points can be identified using various colors, shadings, or textures to identify a cost function value associated with each of the selected portions. Alternatively, or in addition to a color scale or shading display, numerical values can be illustrated for each of the selected or determined target points, entry points, trajectory, or other appropriate data. A graphic representation, especially overlaying or superimposed on image data of the patient 18, can provide an efficient and fast conveyance of information to the user 22.

With additional reference to FIG. 2B, displaying the cost function value of block 120 can include various sub-portions or sub-parts. As specifically illustrated in FIG. 2B, the display of the cost function as an output in block 120 can include selecting a cost function value threshold in block 120a. Selecting a cost function value threshold can include selecting a threshold value that can be used to determine whether or not a particular trajectory is illustrated with the display 12. As discussed further herein, and illustrated in FIGS. 3-5C, various distinct trajectories or trajectory regions can be illustrated with the display 12. The cost function value threshold can determine whether all possible trajectories are illustrated or only whether a subset of those that passes the threshold are displayed with the display 12. The selection of a cost function value threshold in block 120a, can be any appropriate value and can be based on the pre-selected threshold or by input from the user 22.

Selecting an entry point can be performed in block 120b. Selecting an entry point can also identify, optionally, only selected trajectories or trajectory regions. For example, the method 100 can be used to identify all possible trajectories from any anatomical surface to a selected target 164, illustrated in FIG. 3. In block 120b, the number of possible entry points or entry point regions can be limited to a surface of the skull or a partial surface of the skull. For example, if image data is acquired of the patient 18 including the brain 50, the user 22 can identify, as a starting point for the illustration of the display of the trajectories, various specific entry points relative to the brain 50. As illustrated further herein, entry points to reach a target can include or have associated therewith specific trajectories and the selection of them by a user can limit the trajectories or regions illustrated with the display 12. As a specific example, an entry point near an occipital lobe or parietal lobe can be selected as opposed to allowing illustration of trajectories from all possible entry points on the skull relative to the brain 50.

The output can also include a selection of a graphical representation in block 120c. The selection of a graphical representation can include various selections such as the specific selections in block 120d. For example, the graphical representations can include color, grey scale, textures, shading, and other graphical illustrations to be displayed with the display 12. Also, as discussed above, the selection can allow the user 22 to select providing a different representation for different cost function values, different portions of selected trajectories, and the like.

A type of trajectory can also be selected, in addition to the selection of the threshold, entry points, and graphic representations. For example, a distinct trajectory can be selected in block 120e. Distinct trajectories can include trajectories that are substantially illustrated as a single line or a path to be traversed by a single instrument. Distinct trajectories are illustrated in FIG. 5A and the display window 153 in FIG. 4. The distinct trajectories can illustrate distinct paths that will be passed as the instrument 14 moves from the entry point 166d, to the target 164.

Figure 3:
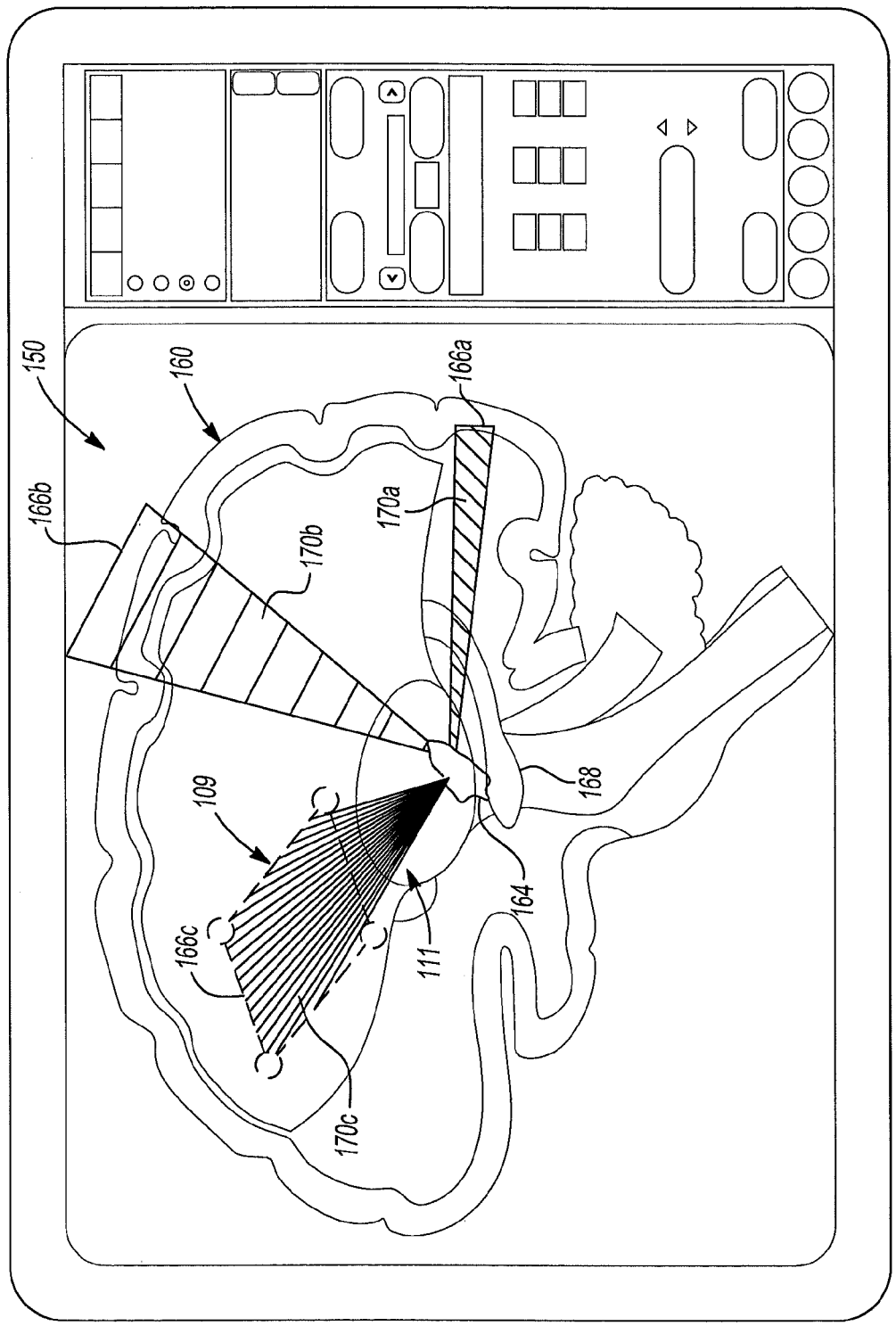
FIG. 3 is an exemplary illustration of a graphical representation of a trajectory.
Figure 5A:
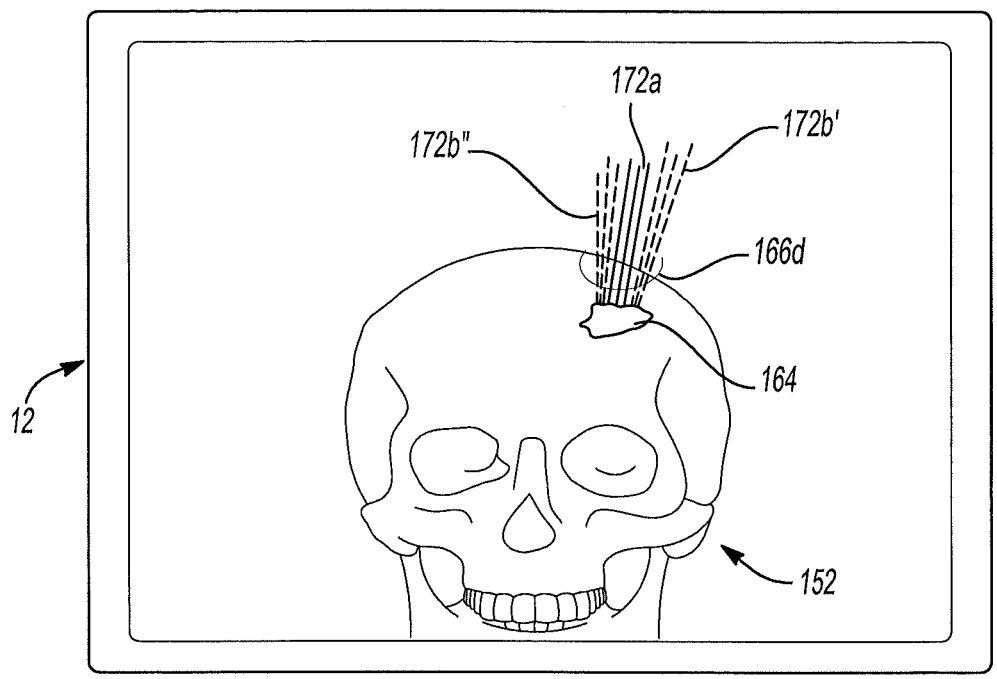
FIGS. 5A and 5B illustrate graphical representations of trajectories, according to various embodiments.
Figure 5B:
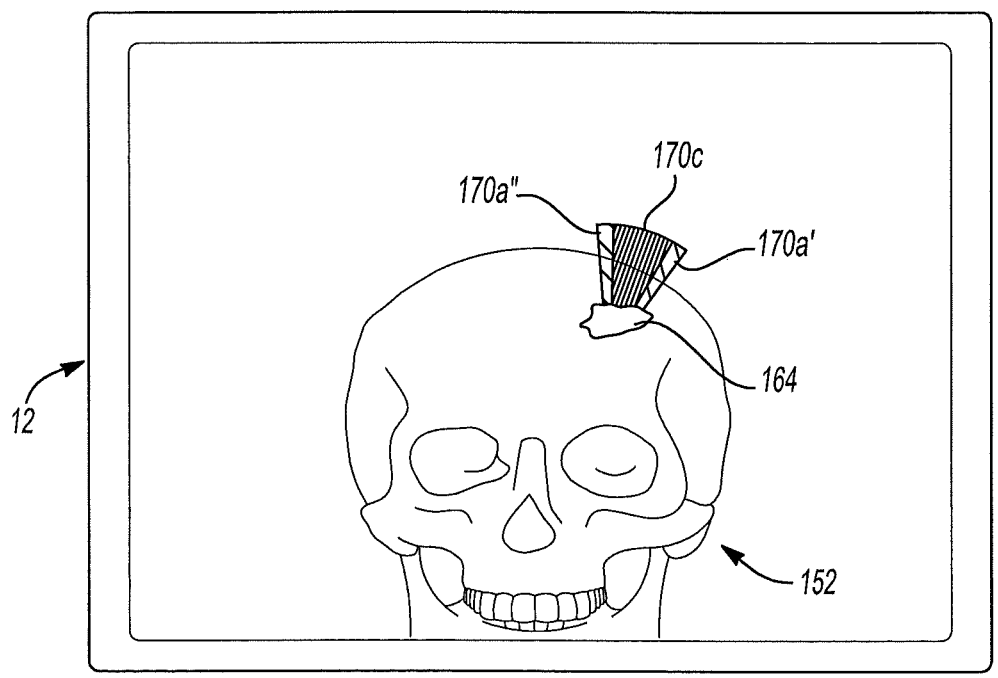

A region can also be displayed by selection in block 120f. The region selected in block 120f, can include regions as illustrated in FIGS. 3 and 5B. The region can identify an area which can encompass more than one possible trajectory. The region can include one or more regions based upon cost function values illustrated, as discussed further herein. The region illustrated can be selected to allow for greater variability of specific surgical occurrences, such as placement of an instrument guide, movement of the instrument, brain or anatomical shift, and other various factors.

A distinct-to-region selection can also be made in block 120g. The distinct-to-region selection in block 120g, can include displaying the cost function value illustrations of all trajectories identified through the entry point selections, threshold selection, and other inputs in block 120h. A sub-plurality or selected plurality of all of the trajectories illustrated in block 120h, can be selected in block 120i.

Each of the trajectories selected in block 120i, can include the same or similar cost function values. Alternatively, different cost function values can be provided for each of the selected trajectories in block 120i. Also, the user 22 or the system 38 can define or select a range for inclusion in a region defined in block 120j. For example, the user can select that a cost function value X plus-or-minus value Y (i.e. 1+/−0.5) should be included in a defined region. The system 38 can then identify all trajectories and place them in a defined region, defined in block 120j. Thus, the selection of trajectories in block 120i, can include selecting specific trajectories, selecting a cost function value, or selecting a cost function value range.

In block 120j, a region can then be defined including the selected sub-plurality of all of the trajectories in block 120i. The region defined in block 120j, can be displayed including a representation of the cost function value that includes an average or weighted average of all of the selected trajectories. Therefore, for example, if the multiple trajectories selected in block 120i, include different cost function values, the cost function values can be averaged in a region identified in block 120j, including the average of the cost function values or an aggregate of the cost function values for display with the display 12. Therefore, an area defining more than one trajectory can be illustrated for use during a procedure. The display 12 can then include a display of the region in block 120k, based upon the selected multiple trajectories.

In addition, a region-to-distinct selection can be made in block 120l. The region-to-distinct can be substantially reverse of the distinct-to-region and can be used to identify specific trajectories within a selected region. For example, as illustrated in FIG. 3, a region of trajectories can be illustrated. The region can then have a sub-portion of the region selected in block 120m. The user 22 or the system 38 can identify a portion of the region based on various inputs. For example, the user 22 may select to position the instrument 14 within a selected portion of the identified entry point area relative to the patient 18. The display output in block 120 can then include a display of distinct trajectories within the region in block 120n. The display of distinct trajectories can allow the user 22 to identify a specific location for positioning a guide instrument, the selection of a specific instrument 14, and for identification of the possibility of one specific trajectory including a higher or better cost function value as opposed to an aggregate of the multiple trajectories within the region.

The various portions of the procedure 100 can be generally automatic. In other words, the procedure determined in block 106 can be determined by a user and then target points, entry points and trajectories and cost value determinations can be based upon calculations of the cost function by a processing system. It will be understood that target points or entry points can be input by a user and then the processor system can further determine the cost function value for the trajectories determined between the selected target points in block 110 and the selected entry points in block 112. Nevertheless, once a cost function value is displayed for each of the determined trajectories, a trajectory can be determined in block 122. The determination or selection of the trajectory in block 122 can be substantially automatic and pass through block 124 or manual and pass through block 126.

An automatic selection of a trajectory can be based upon the cost function value calculated in block 118. Therefore, an automatic trajectory selection in block 124 can include the selection of the trajectory including the best cost function value. The substantially automatically determination in block 124 can be based solely on the determination by a processor system.

The determination of the trajectory can also be substantially manual in block 126. The manual selection of a trajectory in block 126 can be based upon the experience and knowledge of a user or surgeon viewing the various cost function values of the trajectories displayed in block 120 and the determined trajectories in block 114. Therefore, the user in manually selecting a trajectory in block 126, can use knowledge and experience of the user in conjunction with a determined cost function value for each of the determined trajectories. It will be understood, however, that a user can also identify that only selected trajectories should be illustrated. For example, a user may identify that only a trajectory including a cost function value above a selected threshold be illustrated for selection by a user in block 126.

After a trajectory is selected in block 122, any appropriate procedure may optionally be performed in block 128. For example, heart lead placement, deep brain stimulation lead placement, pedicle screw placement can be performed. The procedure can be performed with navigation, as discussed above, to navigate an instrument relative to the selected trajectory from block 122. It may also be selected, however, to simply plan a procedure and a selection of a trajectory in block 122 can lead to the end of the method in block 130. Therefore, it will be understood that the method can include a planning and a performing of a procedure.

Various planning procedures or display systems include those disclosed in U.S. patent application Ser. No. 11/584,814, filed Oct. 20, 2006, now published as U.S. Pat. App. Pub. 2008/0123923 on May 29, 2008; U.S. patent application Ser. No. 11/584,813, filed Oct. 20, 2006, now published as U.S. Pat. App. Pub. 2008/0123922 on May 29, 2008; U.S. patent application Ser. No. 11/584,423, filed Oct. 20, 2006, now published as U.S. Pat. App. Pub. 2008/0123921 on May 29, 2008; U.S. patent application Ser. No. 11/584,422, filed Oct. 20, 2006, now published as U.S. Pat. App. Pub. 2008/0097187 on Apr. 24, 2008; U.S. patent application Ser. No. 11/683,796, filed Mar. 8, 2007, now published as U.S. Pat. App. Pub. 2008/0081982 on Apr. 3, 2008; and patent application Ser. No. 11/409,499, filed Apr. 21, 2006, now published as U.S. Pat. App. Pub. 2007/0249911 on Oct. 25, 2007; all of which are incorporated herein by reference.

Figure 4:
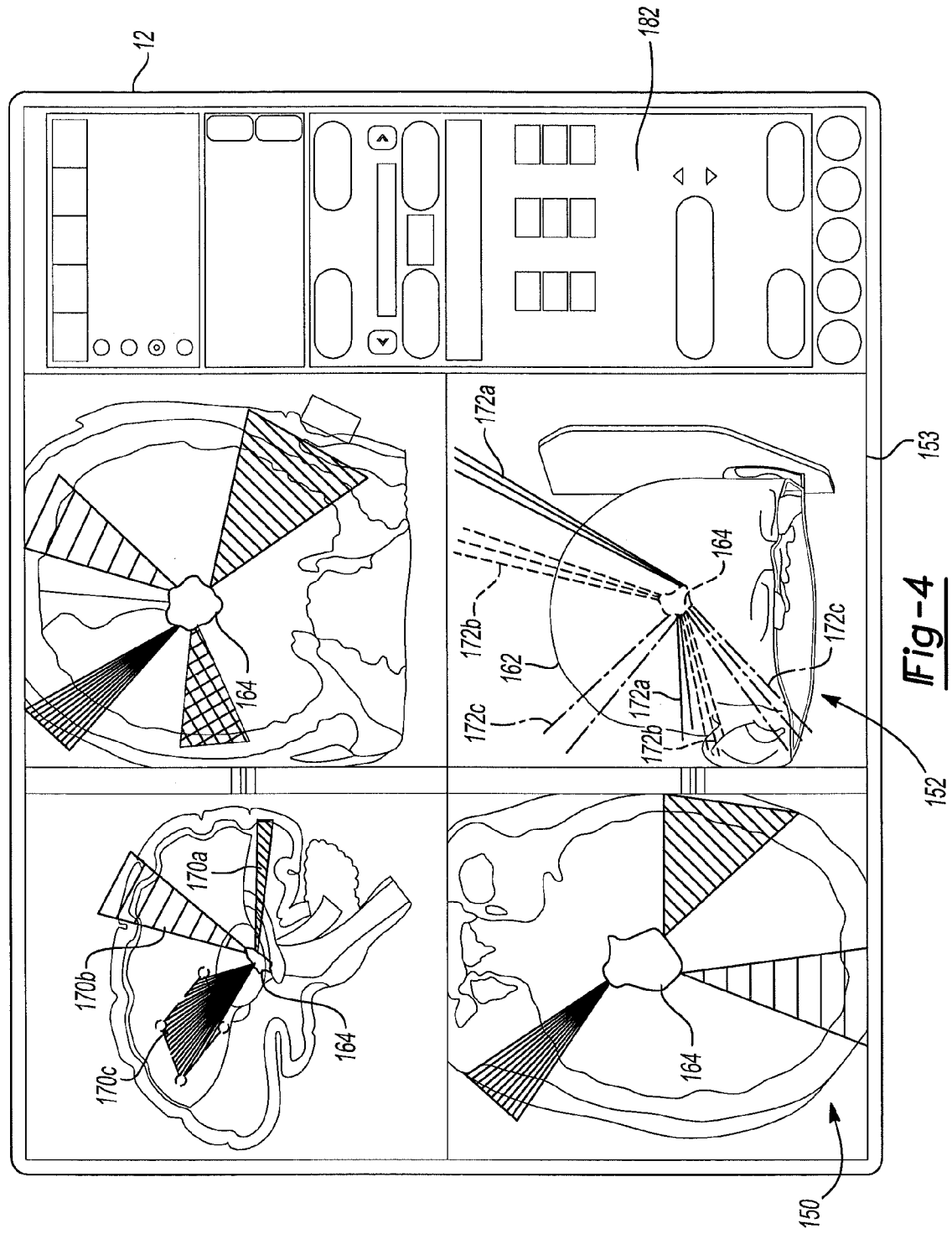
FIG. 4 is an exemplary illustration of a graphical representation of a trajectory.

With reference to FIGS. 3 and 4, image data can be acquired, such as in block 106. An image data 150 can include any appropriate image data, such as a two dimensional, three dimensional, or a four dimensional scan of a patient. The two or three dimensional image data can be used to illustrate the cost function value for various portions, such as entry points, target points, or trajectories.

With initial reference to FIG. 3, the two dimensional image data 150 can illustrate a plurality of types of graphics representing the cost function values. The image data 150 can include a two dimensional slice of a neural region or brain 160. The image data 150 can also include or be representative of external features, such as a skull 162, illustrated in FIG. 4. Nevertheless, the image data 150 can also include a target region 162 that can be any appropriate size or dimension. The target 164 can be identified by the processor system or, in the alternative or in addition, can be identified by a user including a surgeon. Also, entry regions 166a, 166b, 166c, can be illustrated. The entry regions 166a-166c, can be any appropriate region identified relative to the target 164 that allows an instrument to move from the entry region 166a-166c, to the target 164. It will be understood that trajectories identified to traverse from the entry regions 166a-166c, to the target 164 can be straight, curved, or any combination thereof.

The image data can be segmented and anatomical features can be identified, such as an anatomical feature 168. Other processes can also include edge detection and partial segmentation to identify or determine anatomical portions. The anatomical feature 168 can include various features such as fiber tracts, sulci, vascular regions, white matter, grey matter. The anatomical feature 168 can be automatically identified or identified by the user 22.

As discussed in relation to FIGS. 2A and 2B, a cost function can be determined in block 116 for trajectories that may traverse near or through any of the identified anatomical feature 168. For example, a cost function can be determined regarding for each of the entry regions 166a, -166c, the anatomical feature 168, or other segmented or identified areas in the image data 150. The processor, either alone or in combination with the user 22, can also identify a plurality of trajectories from each of the entry points 166a-166c, to the target 164.

The plurality of trajectories can be identified as various regions of trajectories 170a-170c. The regions of trajectories 170a-170c, can be illustrated on the image data or superimposed on the image data 150 as a graphical representation of a cost function value associated with the region of the trajectories 170a-170c. It will be further understood, each individual trajectory can be illustrated with an associated graphical representation identifying the cost function value relating thereto, as illustrated in FIG. 4.

Regardless of whether individual trajectories are shown or trajectory regions are shown, the different regions 170a, -170c, can include different graphical representations of their associated cost function values. For example, region 170a, can be hatched with a selected or specific pattern to illustrate a selected cost function value, such as a highly negative or prohibitive cost function value. Region 170b, can be slightly less darkly hatched or have a different pattern than region 170a, to illustrate a less prohibitive cost function value. Finally, region 170c, can include straight lines or a different pattern to illustrate the lowest prohibitive cost function value. Graphical representations, however, can include different colors, blink or flash rates, textures, shading, brightness, contrast, hatching or cross-hatching patterns, etc.

A three dimensional image data 152 shown in window 153 can also include distinct trajectories, such as distinct lines superimposed thereon. The trajectory lines can include groups 172a-172c, that are illustrated as solid lines, dashed lines, or dash-dot lines. Again, the different graphical representations can show varying degrees of cost function value for the different determined trajectories.

As further illustrated in FIG. 4, different distinct trajectories or cost function values need not be separated by a great distance. For example, cost function value illustrations can be positioned substantially near each other such as illustrated in solid lines 172a, dashed lines 172b, and dashed dot lines in 172c. Therefore, even within a large region, distinct trajectories can include different cost function values that can be illustrated on the display 12 to illustrate the different cost function values.

Regardless of the type of display, the same graphical representation can be used to illustrate the same cost function value. In addition, the graphical representations can illustrate only a portion of a trajectory or region of trajectories. Thus, the user 22 can select or the system can illustrate a cost function value for only a portion of a trajectory. Also, the system can determine and/or illustrate, if selected, a cost function value of different portions of a single region or distinct trajectory. For example, a high cost may be associated with a selected region or distinct trajectory nearer the target 164 than near the entry point 166. This can be illustrated by altering the representation of the distinct trajectory or region over its length or dimension.

In addition, the display 12 can include further information, such as the numerical representation 182 of the cost function value, of one or more of the trajectories or trajectory regions. Therefore, the output of the system or the display of the cost function value from block 120 can be graphical and numerical. In addition, rather than simply providing a shading, a color representation can be provided for different cost values. In addition, a user can determine what type of graphical representation the user would prefer to view for display as a superimposition on the image data 150, 152 on the display screen 12. Also, auditory or tactical outputs can be provided in addition to a visual display or complimentary thereto.

With additional reference to FIGS. 5A and 5B, the display 12 can display the image data 152, which can include a three dimensional image data, and distinct or region trajectories relative to the target 164 from an entry point or area 166d. As illustrated in FIG. 5A, distinct trajectories can include the dashed trajection lines 172b', 172b" and solid trajectory lines 172a. The cost function values associated with the dashed or solid distinct trajectory lines 172b', 172b", 172a, can illustrate the relative or absolute cost function values (whether more or less) of each of the distinct lines. Further, as illustrated in FIG. 5A, there can be a first area of distinct trajectory lines that have a selected cost function values 172b' and a second area of distinct trajectory lines that have the same or similar cost function values 17b". These can be separated by a third set of distinct cost function value lines that include the value illustrated by the solid lines 172a. As discussed above, in relation to FIG. 2B, distinct cost trajectories can be illustrated with their associated cost function values. Alternatively, the cost function values can be illustrated as regions, as illustrated in FIG. 5B.

A region can include an area defined by the extent of distinct trajectories that include the same or substantially similar cost function values. For example, a lightly shaded region 170a' and a similarly lightly shaded region 170a" can be illustrated relative to a darker region 170c. The lightly shaded regions 170a', 170a" can relate to the distinct trajectories of similar cost function values 172b', 172b". In addition, the region 170c, can relate to the distinct trajectories 172a. Also, as discussed above, the regions can include a plurality of distinct trajectories having a range of cost function values. In other words, the region and its associate cost function value can relate to an aggregate of the included distinct trajectories.

As discussed in relation to FIG. 2B, a user can select to illustrate either regions or distinct trajectories based upon the user selection, information to be provided to the user, or other appropriate selections. In addition, the user can select to alter the display from the display in FIG. 5A, including distinct trajectories to the display in FIG. 5B, including regions, and vice versa. The user 22 can select the number and type of trajectories illustrated on the display 12.

Providing a region, as illustrated in FIG. 5B, can illustrate or convey an aggregate cost function value for a plurality of distinct trajectories. A region of distinct trajectories can be selected by the user by selecting a region threshold and the system 38 can determine which trajectories, in the aggregate or average, meet the threshold. The various regions, identified in the display in FIG. 5B, therefore, can identify regions that meet the aggregate threshold. A region can also provide for a larger area for traversal by the instrument 14 during a surgical procedure. Accordingly, a region can allow for greater variability in placement of a guide instrument and movement of the instrument 14.

Figure 5C:
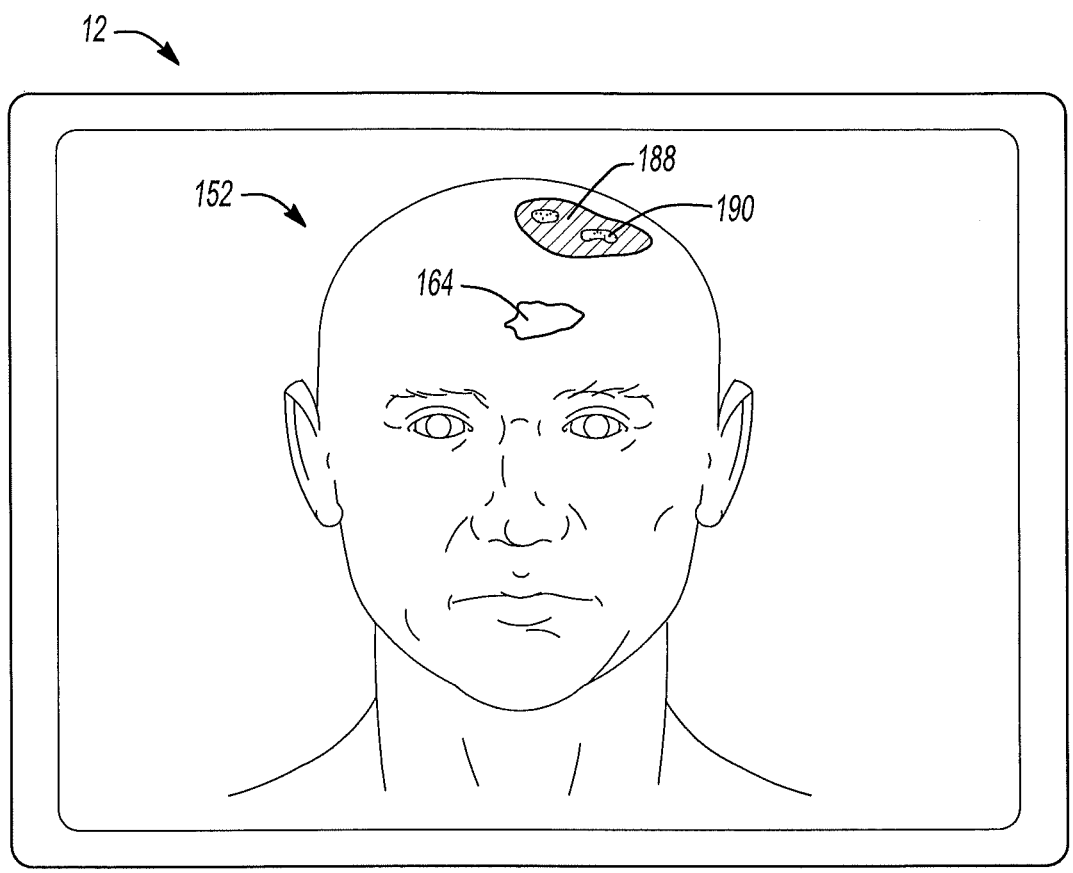
FIG. 5C illustrates a graphical representation of entry points or areas, according to various embodiments.

In addition to, or distinct from, one or more trajectories starting or entry points can be illustrated as a region or group, as illustrated in FIG. 5C. The trajectories, either individually or as an aggregate, can illustrate the cost function value of trajectories from an entry point to a target, such as the target 164. It can be selected, however, to illustrate only the entry points for various trajectories on a surface of the patient, as illustrated in FIG. 5C. For example, a plurality or aggregate of entry points can be illustrated with or as the associated cost function values. The information can be shown as the entry points only or in conjunction with associate trajectories from the entry points to the target 164.

For example, a first entry point area 188 can have a first color, texture, or the like to illustrate a first cost function value. A second area 190 can include a second or different color, shading, or the like to illustrate a second cost function value. Therefore, including two or more colors, textures, shadings, blinking rates, or other graphical representations can illustrate to the user 22 an associated cost function value with one or more entry points.

It will be further understood that trajectories can be illustrated from the entry areas 188, 190 to the target 164 either during planning or during a surgical procedure for navigation. Nevertheless, the entry point areas 188, 190 can be illustrated for selection of an entry point in planning or performing a procedure.

It will be further understood that the entry point areas 188, 190 need not include sharp or distinct boundaries. For example, particularly when illustrating aggregate or average cost function values, edges between different areas may include various shades of colors or other graphical representations separating or illustrating different cost function values. Accordingly, the user 22 can view the display 12 and understand a cost function value may change gradually or sharply from one position to another.

It will also be understood that the system 38 or the navigation system 10, can provide feedback information to the user 22 during navigation of the procedure with the determined or planned trajectories or region trajectories. Feedback can include a sound, such as one admitted by a speaker. Other feedback can include visual feedback or tactile feedback to indicate whether or not the instrument 14 being tracked is traversing the selected trajectory or region.

The system can display on the display 12 any selected number or all of the trajectories determined to reach the target 164. In addition, a user can select to represent only a selected trajectory. For example, a threshold value can be identified for trajectories and only the trajectories including or surpassing the threshold value can be displayed on the display 12. Therefore, one will understand that the representation of the trajectories can be shown on the display 12 in any appropriate manner and in any appropriate number. For example, all possible trajectories from an entry point to a target point can be illustrated with their associated cost function values. The user 22 can alone, or in combination with another processor, select the trajectory.

It will be further understood that any appropriate image data can be displayed on the display 12. For example, image data of a cardiac region can be displayed, image data of a spinal region, and any other appropriate image data can be provided. Accordingly, illustrating or representing trajectories can be provided for any appropriate procedure and a neural procedure is illustrated simply as an example.

Further areas of applicability of the present teachings will become apparent from the detailed description provided above. It should be understood that the detailed description and specific examples, while indicating various embodiments, are intended for purposes of illustration only and are not intended to limit the scope of the teachings.

What is claimed is:

1. A method of determining a cost function value for a selected procedure, comprising:
   accessing image data of a patient;
   determining at least one entry point for the procedure;
   determining at least one target for the procedure;
   executing instructions with a processor to:
     determine anatomical features in the accessed image data;
     associate a weight to each of the determined anatomical features;
     associate a weight with each of the at least one entry point and the at least one target point;
     determine a plurality of possible trajectories through an anatomical region of the patient and a position of each trajectory of the determined possible trajectories relative to the determined anatomical features;
     associate each trajectory of the determined plurality of trajectories with the at least one entry point and the at least one target point;
     determine a cost function for each trajectory of the possible trajectories based at least in part on the position of each of the possible trajectories relative to the determined anatomical features and the associated weight of the determined anatomical features, the trajectory and the associated at least one entry point and the at least one target;
     determine a cost function value for each trajectory of the possible trajectories based on the determined cost function for the possible trajectories;
     output a representation of the cost function value based upon the determination of the cost function for each trajectory of the plurality of possible trajectories including outputting the representation of the cost function value determined with the cost function incorporating the weight determined for each of the plurality of trajectories, the at least one entry point, and the at least one target point;
   selecting a region that is defined by at least one or a sub-plurality of trajectories of the determined plurality of possible trajectories based upon the output representation of the cost function value, wherein the selected region is used to perform a navigated procedure by moving an instrument along a procedure trajectory with the selected region and wherein the selected region is selected to allow for a greater variability of an instrument placement for the selected procedure; and
   displaying a region cost function value on a human viewable display based on a cost function value of the selected region defined by the at least one or sub-plurality of trajectories of the determined plurality of possible trajectories.

2. The method of claim 1, wherein accessing image data of the patient includes accessing magnetic resonance image data, computer tomography image data, PET image data, functional MRI image data, diffusion tensor image data, x-ray image data, or combinations thereof.

3. The method of claim 2, wherein executing instructions with the processor to determine anatomical features in the accessed image data includes at least one of performing edge detection on the image data, selecting anatomical features in the image data, or performing segmentation of the image data.

4. The method of claim 1, wherein the outputted graphical representation of the cost function value includes at least one of a shaded area, a textured area, a dashed line, a blinking line, a blinking area, a color, or combinations thereof.

5. The method of claim 1, further comprising:
providing an imaging device operable to acquire the accessed image data of the patient.

6. The method of claim 1, further comprising:
tracking the instrument relative to the selected trajectory; and
displaying a representation of the instrument as the instrument is tracked.

7. The method of claim 6, further comprising:
displaying the accessed image data of the patient;
superimposing the selected region on the accessed image data of the patient; and
superimposing a graphical representation of the instrument on the image data relative to the graphical representation of the selected region.

8. The method of claim 7, wherein displaying the region cost function value includes associating a specific graphical representation of the output cost function value with the selected region and superimposing the specific graphical representation on the image data.

9. The method of claim 1, further comprising:
accessing data regarding a patient including at least one patient history or medical statistical data.

10. The method of claim 9, wherein determine the cost function for each trajectory of the possible trajectories further includes evaluating the weighting of the determined anatomical regions relative to each trajectory of the determined plurality of trajectories to determine a plurality of cost functions including at least one cost function for each trajectory of the plurality of the determined trajectories.

11. The method of claim 1, further comprising:
performing a procedure based upon the selected at least sub-plurality of trajectories; and
navigating the procedure with a navigation system.

12. A method of determining a cost function value for a selected procedure, comprising:
determining at least one entry point for the procedure based on an accessed data of a subject;
determining at least one target for the procedure based on the accessed data of the subject;
executing instructions with a processor to:
determine anatomical features in the accessed data;
associate a weight to each of the determined anatomical features;
associate a weight to the at least one entry point;
associate a weight to the at least one target point;
determine a plurality of possible trajectories through an anatomical region of the patient between the determined at least one entry point and the determined at least one target and a position of each trajectory of the determined possible trajectories relative to the determined anatomical features;
associate each trajectory of the determined plurality of trajectories with the at least one entry point and the at least one target point;
determine a cost function for each trajectory of the possible trajectories based at least in part on the position of each of the possible trajectories relative to the determined anatomical features and the associated weight of the determined anatomical features, the trajectory, the at least one entry point, and the at least one target of the trajectory;
determine a cost function value for each trajectory of the plurality of possible trajectories based on the determined cost function for each trajectory of the plurality of possible trajectories;
output a representation of the cost function value based upon the determination of the cost function for each trajectory of the plurality of possible trajectories including outputting a graphical representation of the cost function value determined with the cost function incorporating the weight determined for each of the trajectories, the at least one entry point, and the at least one target point;
selecting at least one trajectory or a sub-plurality of trajectories of the determined plurality of possible trajectories based upon the output representation of the cost function value, wherein the selected at least one or a sub-plurality of trajectories of the determined plurality of possible trajectories is used to perform a navigated procedure by moving an instrument along a procedure trajectory based on the selected at least one or a sub-plurality of trajectories of the determined plurality of possible trajectories; and
displaying the output representation of the cost function value on a human viewable display.

13. The method of claim 12, wherein selecting the at least one trajectory or sub-plurality of trajectories of the determined plurality of possible trajectories includes selecting a region.

14. The method of claim 13, further comprising:
determine a region cost function value based on the cost function value of the at least one trajectory or sub-plurality of trajectories of the determined plurality of possible trajectories.

15. The method of claim 14, wherein the selected region is selected to allow for a greater variability of placement of an instrument for the selected procedure.

16. The method of claim 12, further comprising:
accessing image data of the patient including accessing magnetic resonance image data, computer tomography image data, PET image data, functional MRI image data, diffusion tensor image data, x-ray image data, or combinations thereof.

17. The method of claim 12, wherein executing instructions with a processor to determine anatomical features in the accessed data includes at least one of performing edge detection on image data, selecting anatomical features in the image data, or performing segmentation of the image data.

18. The method of claim 12, wherein the outputted graphical representation of the cost function value includes at least one of a shaded area, a textured area, a dashed line, a blinking line, a blinking area, a color, or combinations thereof.

19. The method of claim 12, further comprising:
providing an imaging device operable to acquire image data of the patient.

20. The method of claim 12, further comprising:
tracking the instrument relative to the selected at least one trajectory or a sub-plurality of trajectories of the determined plurality of possible trajectories; and
displaying a representation of the instrument as the instrument is tracked.

21. The method of claim 12, further comprising:
displaying accessed image data of the subject;

superimposing the selected at least one trajectory or a sub-plurality of trajectories of the determined plurality of possible trajectories on the accessed image data of the patient; and superimposing a graphical representation of the instrument on the image data relative to the graphical representation of the selected at least one trajectory or a sub-plurality of trajectories of the determined plurality of possible trajectories.

22. The method of claim 12, further comprising:
accessing data regarding a patient including at least one patient history or medical statistical data.

23. The method of claim 22, wherein determine the cost function for each trajectory of the possible trajectories further includes evaluating the weighting of the determined anatomical regions relative to each trajectory of the determined plurality of trajectories to determine a plurality of cost functions including at least one cost function for each trajectory of the plurality of the determined trajectories.

* * * * *